(12) United States Patent
Giles

(10) Patent No.: US 8,334,502 B2
(45) Date of Patent: Dec. 18, 2012

(54) APPARATUS COMPRISING AN ION MOBILITY SPECTROMETER

(75) Inventor: Kevin Giles, Cheshire (GB)

(73) Assignee: Micromass UK Limited, Manchester (GB)

( * ) Notice: Subject to any disclaimer, the term of this patent is extended or adjusted under 35 U.S.C. 154(b) by 0 days.

(21) Appl. No.: 13/297,791

(22) Filed: Nov. 16, 2011

(65) Prior Publication Data

US 2012/0056084 A1   Mar. 8, 2012

Related U.S. Application Data

(63) Continuation of application No. 12/373,341, filed as application No. PCT/GB2007/002622 on Jul. 12, 2007, now Pat. No. 8,076,636.

(60) Provisional application No. 60/827,892, filed on Oct. 3, 2006.

(30) Foreign Application Priority Data

Jul. 13, 2006 (GB) .................................. 0613900.0
Sep. 14, 2006 (GB) .................................. 0618110.1

(51) Int. Cl.
*B01D 59/44* (2006.01)
*H01J 49/40* (2006.01)

(52) U.S. Cl. ........ 250/282; 250/281; 250/290; 250/291; 250/292; 250/288

(58) Field of Classification Search .................. 250/281, 250/282, 287, 288, 290, 291, 292
See application file for complete search history.

(56) References Cited

U.S. PATENT DOCUMENTS

| | | | |
|---|---|---|---|
| 4,797,554 A | | 1/1989 | Blanchard et al. |
| 5,304,797 A | * | 4/1994 | Irie et al. ........................ 250/287 |
| 6,774,360 B2 | * | 8/2004 | Guevremont et al. ......... 250/288 |
| 6,884,995 B2 | * | 4/2005 | Bateman et al. ............... 250/281 |
| 7,091,481 B2 | * | 8/2006 | Miller et al. ................... 250/288 |
| 7,138,626 B1 | * | 11/2006 | Karpetsky ....................... 250/288 |
| 7,279,680 B2 | * | 10/2007 | Miller et al. ................... 250/288 |

(Continued)

FOREIGN PATENT DOCUMENTS

GB         2421843          7/2006

(Continued)

OTHER PUBLICATIONS

PCT/ISA/237, Written Opinion for PCT/GB2007/002622, dated Oct. 19, 2007.

(Continued)

*Primary Examiner* — David A Vanore
(74) *Attorney, Agent, or Firm* — Diederiks & Whitelaw, PLC

(57) ABSTRACT

A mass spectrometer is disclosed comprising a first chamber and a second chamber. The second chamber is located downstream of the first chamber and an inter-chamber aperture is provided between the two chambers. An ion guide is located in the first chamber and an ion mobility spectrometer is located in the second chamber. Helium gas is provided to the first chamber. As ions are accelerated towards the ion mobility spectrometer from a relatively low pressure region they pass initially into the first chamber. The helium gas provided in the first chamber minimizes ion fragmentation and ion discrimination effects as ions are accelerated into a relatively high pressure region. The ions are then transmitted by the ion guide and are subsequently transmitted to the ion mobility spectrometer located in the second chamber.

20 Claims, 2 Drawing Sheets

U.S. PATENT DOCUMENTS

| | | |
|---|---|---|
| 7,820,966 B2 | 10/2010 | Bateman |
| 2002/0175278 A1* | 11/2002 | Whitehouse .................. 250/281 |
| 2003/0020012 A1 | 1/2003 | Guevremont |
| 2003/0038235 A1* | 2/2003 | Guevremont et al. ........ 250/287 |
| 2003/0057369 A1* | 3/2003 | Guevremont et al. ........ 250/286 |
| 2003/0101795 A1* | 6/2003 | Makihara et al. .............. 73/23.2 |
| 2006/0249671 A1* | 11/2006 | Karpetsky .................... 250/288 |
| 2007/0114382 A1* | 5/2007 | Clemmer et al. ............. 250/287 |
| 2009/0108195 A1* | 4/2009 | Guevremont et al. ........ 250/282 |
| 2010/0044561 A1* | 2/2010 | Giles ........................... 250/282 |

FOREIGN PATENT DOCUMENTS

| | | |
|---|---|---|
| WO | WO 02/086946 | 10/2002 |
| WO | WO 02/096805 | 12/2002 |

OTHER PUBLICATIONS

PCT/ISA/210, International Search Report for PCT/GB2007/002622, dated Oct. 19, 2001.

* cited by examiner

APPARATUS COMPRISING AN ION MOBILITY SPECTROMETER

CROSS REFERENCE TO RELATED APPLICATIONS

This application is a continuation of U.S. patent application Ser. No. 12/373,341 filed Aug. 25, 2009, which is the National Stage of International Application No. PCT/GB2007/002622, filed Jul. 12, 2007 and designating the United States, which claims benefit of and priority to U.S. Provisional Patent Application No. 60/827,892, filed Oct. 3, 2006, United Kingdom Patent Application No. 0613900.0, filed Jul. 13, 2006, and United Kingdom Patent Application No. 0618110.1, filed Sep. 14, 2006. The entire contents of these applications are incorporated herein by reference.

BACKGROUND OF THE INVENTION

The present invention relates to apparatus comprising an ion mobility spectrometer, a mass spectrometer, a method of ion mobility spectrometry and a method of mass spectrometry.

Ion mobility spectrometers ("IMS") are known which are provided at sub-ambient pressure conditions within the vacuum chamber of a mass spectrometer. Typically, the chamber housing the ion mobility spectrometer is maintained at a gas pressure in the range of 0.1 to 10 mbar. The chamber housing the ion mobility spectrometer must be provided in a differentially pumped vacuum chamber in order to minimise gas loading of a mass analyser which is arranged downstream of the ion mobility spectrometer in a separate vacuum chamber. Depending upon the location of the ion mobility spectrometer in the overall mass spectrometer, ions may have passed through a region of relatively low pressure prior to entry into the chamber housing the ion mobility spectrometer. If ions pass through a region of relatively low pressure immediately prior to the chamber housing the ion mobility spectrometer then it is necessary to drive the ions into the chamber housing the ion mobility spectrometer against a significant outflow of gas from the chamber. The requirement to drive ions into the chamber housing, the ion mobility spectrometer against a significant outflow of gas can be particularly problematic especially if some of the ions are relatively fragile or have relatively low mobilities since the use of a relatively high electric field to drive the ions into the relatively high pressure chamber can lead to undesired effects such as ion fragmentation and/or ion mobility effects.

It is therefore desired to provide an improved apparatus comprising an ion mobility spectrometer.

BRIEF SUMMARY OF THE INVENTION

According to an aspect of the present invention there is provided an apparatus comprising:

a first chamber;

a second chamber located downstream of the first chamber;

an ion mobility spectrometer or separator located in the second chamber;

a device for providing a first gas or mixture of gases to the first chamber, the first gas or mixture of gases having a first average density or molecular weight $M_1$; and a device for providing a second gas or mixture of gases to the second chamber, the second gas or mixture of gases having a second average density or molecular weight $M_2$, wherein $M_1 < M_2$.

The ratio $M_2/M_1$ is preferably selected from the group consisting of: (i) $\geq 1.1$; (ii) $\geq 1.5$; (iii) $\geq 2.0$; (iv) $\geq 3.0$; (v) $\geq 4.0$; (vi) $\geq 5.0$; (vii) $\geq 6.0$; (viii) $\geq 7.0$; (ix) $\geq 8.0$; (x) $\geq 9.0$; (xi) $\geq 10.0$; (xii) $\geq 11.0$; (xiii) $\geq 12.0$; (xiv) $\geq 13.0$; (xv) $\geq 14.0$; (xvi) $\geq 15.0$; (xvii) $\geq 16.0$; (xviii) $\geq 17.0$; (xix) $\geq 18.0$; (xx) $\geq 19.0$; (xxi) $\geq 20.0$; (xxii) $\geq 25.0$; (xxiii) $\geq 30.0$; (xxiv) $\geq 35.0$; (xxv) $\geq 40.0$; (xxvi) $\geq 45.0$; (xxvii) $\geq 50.0$; (xviii) $\geq 55.0$; (xxix) $\geq 60.0$; (xxx) $\geq 65.0$; and (xxxi) $\geq 70.0$. According to an embodiment, the ratio $M_2/M_1$ may be selected from the group consisting of: (i) 1-2; (ii) 2-3; (iii) 3-4; (iv) 4-5; (v) 5-6; (vi) 6-7; (vii) 7-8; (viii) 8-9; (ix) 9-10; (x) 10-11; (xi) 11-12; (xii) 12-13; (xiii) 13-14; (xiv) 14-15; (xv) 15-16; (xvi) 16-17; (xvii) 17-18; (xviii) 18-19; (xix) 19-20; (xx) 20-25; (xxi) 25-30; (xxii) 30-35; (xxiii) 35-40; (xxiv) 40-45; (xxv) 45-50; (xxvi) 50-55; (xxvii) 55-60; (xxviii) 60-65; (xxix) 65-70; and (xxx) >70.

The first chamber preferably comprises a housing having an ion inlet aperture and a first gas outlet. The apparatus preferably further comprises an inter-chamber aperture between the first chamber and the second chamber.

The first gas or mixture of gases preferably comprises one or more gases selected from the group consisting of: (i) helium; (ii) hydrogen; (iii) neon; (iv) methane; (v) ammonia; (vi) nitrogen; (vii) argon; (viii) xenon; (ix) air; and (x) SF6 or sulphur hexafluoride.

According to an embodiment, the first gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% helium.

According to an embodiment, the first gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% hydrogen.

According to an embodiment, the first gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% neon.

According to an embodiment, the first gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% methane.

According to an embodiment, the first gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% ammonia.

According to an embodiment, the first gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% nitrogen.

According to an embodiment, the first gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% argon.

According to an embodiment, the first gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% xenon.

According to an embodiment, the first gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% air.

According to an embodiment, the first gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% SF6 or sulphur hexafluoride.

The first gas or mixture of gases is preferably provided at a pressure selected from the group consisting of: (i) <0.1 mbar;

(ii) ≧0.1 mbar; (iii) ≧0.2 mbar; (iv) ≧0.3 mbar; (v) ≧0.4 mbar; (vi) ≧0.5 mbar; (vii) ≧0.6 mbar; (viii) ≧0.7 mbar; (ix) ≧0.8 mbar; (x) ≧0.9 mbar; (xi) ≧1.0 mbar; (xii) ≧1.1 mbar; (xiii) ≧1.2 mbar; (xiv) ≧1.3 mbar; (xv) ≧1.4 mbar; (xvi) ≧1.5 mbar; (xvii) ≧1.6 mbar; (xviii) ≧1.7 mbar; (xix) ≧1.8 mbar; (xx) ≧1.9 mbar; (xxi) ≧2.0 mbar; (xxii) ≧3.0 mbar; (xxiii) ≧4.0 mbar; (xxiv) ≧5.0 mbar; (xxv) ≧6.0 mbar; (xxvi) ≧7.0 mbar; (xxvii) ≧8.0 mbar; (xxviii) ≧9.0 mbar; and (xxix) ≧10.0 mbar. The first gas or mixture of gases is preferably provided at a pressure selected from the group consisting of: (i) 0.1-0.5 mbar; (ii) 0.5-1.0 mbar; (iii) 1.0-1.5 mbar; (iv) 1.5-2.0 mbar; (v) 2.0-2.5 mbar; (vi) 2.5-3.0 mbar; (vii) 3.0-3.5 mbar; (viii) 3.5-4.0 mbar; (ix) 4.0-4.5 mbar; (x) 4.5-5.0 mbar; (xi) 5.0-5.5 mbar; (xii) 5.5-6.0 mbar; (xiii) 6.0-6.5 mbar; (xiv) 6.5-7.0 mbar; (xv) 7.0-7.5 mbar; (xvi) 7.5-8.0 mbar; (xvii) 8.0-8.5 mbar; (xviii) 8.5-9.0 mbar; (xix) 9.0-9.5 mbar; and (xx) 9.5-10.0 mbar.

According to an embodiment, the first chamber has a length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

The apparatus preferably further comprises a first ion guide comprising a plurality of electrodes located in the first chamber. The first ion guide preferably has a length selected from the group consisting of: (i) <20 mm; (ii) 20-40 min; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

The first ion guide may comprise:
(i) a multipole rod set or a segmented multipole rod set;
(ii) an ion tunnel or ion funnel; or
(iii) a stack or array of planar, plate or mesh electrodes.

The multipole rod set or the segmented multipole rod set preferably comprises a quadrupole rod set, a hexapole rod set, an octapole rod set or a rod set comprising more than eight rods.

The ion tunnel or ion funnel preferably comprises a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area. At least 5%, 10%, 15%, 20%, 25%, 30%, 35%, 40%, 45%, 50%, 55%, 60%, 65%, 70%, 75%, 80%, 85%, 90%, 95% or 100% of the electrodes preferably have internal diameters or dimensions selected from the group consisting of: (i) ≦1.0 mm; (ii) ≦2.0 mm; (iii) ≦3.0 mm; (iv) ≦4.0 mm; (v) ≦5.0 mm; (vi) ≦6.0 mm; (vii) ≦7.0 mm; (viii) ≦8.0 mm; (ix) ≦9.0 mm; (x) ≦10.0 mm; and (xi) >10.0 mm.

The stack or array of planar, plate or mesh electrodes preferably comprises a plurality or at least 2, 3, 4, 5, 6, 7, 8, 9, 10, 11, 12, 13, 14, 15, 16, 17, 18, 19 or 20 planar, plate or mesh electrodes arranged generally in the plane in which ions travel in use, wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use. The apparatus preferably further comprises AC or RF voltage means for supplying the plurality of planar, plate or mesh electrodes with an AC or RF voltage and wherein adjacent planar, plate or mesh electrodes are supplied with opposite phases of the AC or RF voltage.

The first ion guide preferably comprises a plurality of axial segments or at least 5, 10, 15, 20, 25, 30, 35, 40, 45, 50, 55, 60, 65, 70, 75, 80, 85, 90, 95 or 100 axial segments.

According to an embodiment, the apparatus further comprises transient DC voltage means arranged and adapted to apply one or more transient DC voltages or potentials or one or more transient DC voltage or potential waveforms to electrodes forming the first ion guide in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the first ion guide.

According to an embodiment, the apparatus further comprises AC or RF voltage means arranged and adapted to apply two or more phase-shifted AC or RF voltages to the plurality of electrodes forming the first ion guide in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the first ion guide.

The first ion guide preferably further comprises AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the plurality of electrodes forming the first ion guide in order to confine ions radially within the first ion guide. The AC or RF voltage means is preferably arranged and adapted to supply an AC or RF voltage to the plurality of electrodes forming the first ion guide having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak. The AC or RF voltage means is preferably arranged and adapted to supply an AC or RF voltage to the plurality of electrodes forming the first ion guide having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

Singly charged ions having a mass to charge ratio in the range of 1-100, 100-200, 200-300, 300-400, 400-500, 500-600, 600-700, 700-800, 800-900, 900-1000 or >1000 preferably have a drift or transit time through the first ion guide in the range: (i) 0-10 μs; (ii) 10-20 μs; (iii) 20-30 μs; (iv) 30-40 μs; (v) 40-50 μs; (vi) 50-60 μs; (vii) 60-70 μs; (viii) 70-80 μs; (ix) 80-90 μs; (x) 90-100 μs; (xi) 100-110 μs; (xii) 110-120 μs; (xiii) 120-130 μs; (xiv) 130-140 μs; (xv) 140-150 μs; (xvi) 150-160 μs; (xvii) 160-170 μs; (xviii) 170-180 μs; (xix) 180-190 μs; (xx) 190-200 μs; (xxi) 200-210 μs; (xxii) 210-220 μs; (xxiii) 220-230 μs; (xxiv) 230-240 μs; (xxv) 240-250 μs; (xxvi) 250-260 μs; (xxvii) 260-270 μs; (xxviii) 270-280 μs; (xxix) 280-290 μs; (xxx) 290-300 μs; and (xxxi) >300 μs.

The apparatus preferably further comprises a device arranged and adapted to maintain at least a portion of the first ion guide at a pressure selected from the group consisting of: (i) <0.1 mbar; (ii) ≧0.1 mbar; (iii) ≧0.2 mbar; (iv) ≧0.3 mbar; (v) ≧0.4 mbar; (vi) ≧0.5 mbar; (vii) ≧0.6 mbar; (viii)

≧0.7 mbar; (ix) ≧0.8 mbar; (x) ≧0.9 mbar; (xi) ≧1.0 mbar; (xii) ≧1.1 mbar; (xiii) ≧1.2 mbar; (xiv) ≧1.3 mbar; (xv) ≧1.4 mbar; (xvi) ≧1.5 mbar; (xvii) ≧1.6 mbar; (xviii) ≧1.7 mbar; (xix) ≧1.8 mbar; (xx) ≧1.9 mbar; (xxi) ≧2.0 mbar; (xxii) ≧3.0 mbar; (xxiii) ≧4.0 mbar; (xxiv) ≧5.0 mbar; (xxv) ≧6.0 mbar; (xxvi) ≧7.0 mbar; (xxvii) ≧8.0 mbar; (xxviii) ≧9.0 mbar; and (xxix) ≧10.0 mbar.

The apparatus preferably further comprises a device arranged and adapted to maintain at least a portion of the first ion guide at a pressure selected from the group consisting of: (i) 0.1-0.5 mbar; (ii) 0.5-1.0 mbar; (iii) 1.0-1.5 mbar; (iv) 1.5-2.0 mbar; (v) 2.0-2.5 mbar; (vi) 2.5-3.0 mbar; (vii) 3.0-3.5 mbar; (viii) 3.5-4.0 mbar; (ix) 4.0-4.5 mbar; (x) 4.5-5.0 mbar; (xi) 5.0-5.5 mbar; (xii) 5.5-6.0 mbar; (xiii) 6.0-6.5 mbar; (xiv) 6.5-7.0 mbar; (xv) 7.0-7.5 mbar; (xvi) 7.5-8.0 mbar; (xvii) 8.0-8.5 mbar; (xviii) 8.5-9.0 mbar; (xix) 9.0-9.5 mbar; and (xx) 9.5-10.0 mbar.

The first ion guide is preferably arranged and adapted to receive a beam of ions and to convert or partition the beam of ions such that at least 1, 2, 3, 4, 5, 6, 7, 8, 9, 10, 11, 12, 13, 14, 15, 16, 17, 18, 19 or 20 separate groups or packets of ions are confined and/or isolated in the first ion guide at any particular time, and wherein each group or packet of ions is preferably separately confined and/or isolated in a separate axial potential well formed in the first ion guide.

A first voltage means is preferably arranged and adapted to create at least 1, 2, 3, 4, 5, 6, 7, 8, 9, 10, 11, 12, 13, 14, 15, 16, 17, 18, 19 or 20 separate axial potential wells which are substantially simultaneously translated along at least 5%, 10%, 15%, 20%, 25%, 30%, 35%, 40%, 45%, 50%, 55%, 60%, 65%, 70%, 75%, 80%, 85%, 90%, 95% or 100% of the length of the first ion guide.

The first ion guide is preferably arranged and adapted to retain and/or confine and/or partition ions which are received by the first ion guide and to translate ions in one or more groups or packets of ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the first ion guide whilst either: (i) substantially maintaining the order and/or fidelity in which ions are received by the first ion guide; and/or (ii) substantially maintaining the composition of ions as one or more groups or packets of ions are translated along the first ion guide.

The first ion guide is preferably arranged and adapted to collisionally cool, substantially thermalise or substantially reduce the kinetic energy of ions within the first ion guide.

The second chamber preferably comprises a housing having a second gas outlet and an ion exit aperture.

The second gas or mixture of gases preferably comprises one or more gases selected from the group consisting of (i) helium; (ii) hydrogen; (iii) neon; (iv) methane; (v) ammonia; (vi) nitrogen; (vii) argon; (viii) xenon; (ix) air; and (x) SF6 or sulphur hexafluoride.

According to an embodiment, the second gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% helium.

According to an embodiment, the second gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% hydrogen.

According to an embodiment, the second gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% neon.

According to an embodiment, the second gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% methane.

According to an embodiment, the second gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% ammonia.

According to an embodiment, the second gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% nitrogen.

According to an embodiment, the second gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% argon.

According to an embodiment, the second gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% xenon.

According to an embodiment, the second gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% air.

According to an embodiment, the second gas or mixture of gases comprises at least 5%, 10%, 15%, 20%, 25%, 30%, 35%, 40%, 45%, 50%, 55%, 60%, 65%, 70%, 75%, 80%, 85%, 90%, 95% or 100% SF6 or sulphur hexafluoride.

The second gas or mixture of gases is preferably provided at a pressure selected from the group consisting of: (i) <0.1 mbar; (ii) ≧0.1 mbar; (iii) ≧0.2 mbar; (iv) ≧0.3 mbar; (v) ≧0.4 mbar; (vi) ≧0.5 mbar; (vii) ≧0.6 mbar; (viii) ≧0.7 mbar; (ix) ≧0.8 mbar; (x) 0.9 mbar; (xi) ≧1.0 mbar; (xii) ≧1.1 mbar; (xiii) ≧1.2 mbar; (xiv) ≧1.3 mbar; (xv) ≧1.4 mbar; (xvi) ≧1.5 mbar; (xvii) ≧1.6 mbar; (xviii) ≧1.7 mbar; (xix) ≧1.8 mbar; (xx) ≧1.9 mbar; (xxi) ≧2.0 mbar; (xxii) ≧3.0 mbar; (xxiii) ≧4.0 mbar; (xxiv) ≧5.0 mbar; (xxv) ≧6.0 mbar; (xxvi) ≧7.0 mbar; (xxvii) ≧8.0 mbar; (xxviii) ≧9.0 mbar; and (xxix) ≧10.0 mbar.

The second gas or mixture of gases is preferably provided at a pressure selected from the group consisting of: (i) 0.1-0.5 mbar; (ii) 0.5-1.0 mbar; (iii) 1.0-1.5 mbar; (iv) 1.5-2.0 mbar; (v) 2.0-2.5 mbar; (vi) 2.5-3.0 mbar; (vii) 3.0-3.5 mbar; (viii) 3.5-4.0 mbar; (ix) 4.0-4.5 mbar; (x) 4.5-5.0 mbar; (xi) 5.0-5.5 mbar; (xii) 5.5-6.0 mbar; (xiii) 6.0-6.5 mbar; (xiv) 6.5-7.0 mbar; (xv) 7.0-7.5 mbar; (xvi) 7.5-8.0 mbar; (xvii) 8.0-8.5 mbar; (xviii) 8.5-9.0 mbar; (xix) 9.0-9.5 mbar; and (xx) 9.5-10.0 mbar.

The second chamber preferably has a length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

The ion mobility spectrometer or separator preferably comprises a gas phase electrophoresis device.

The ion mobility spectrometer or separator preferably comprises:
 (i) a drift tube;
 (ii) a multipole rod set or a segmented multipole rod set;
 (iii) an ion tunnel or ion funnel; or
 (iv) a stack or array of planar, plate or mesh electrodes.

The drift tube preferably comprises one or more electrodes and means for maintaining an axial DC voltage gradient or a substantially constant or linear axial DC voltage gradient along at least 5%, 10%, 15%, 20%, 25%, 30%, 35%, 40%, 45%, 50%, 55%, 60%, 65%, 70%, 75%, 80%, 85%, 90%, 95% or 100% of the axial length of the drift tube.

The multipole rod set preferably comprises a quadrupole rod set, a hexapole rod set, an octapole rod set or a rod set comprising more than eight rods.

The ion tunnel or ion funnel preferably comprises a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area. According to an embodiment, at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) $\leq 1.0$ mm; (ii) $\leq 2.0$ mm; (iii) $\leq 3.0$ mm; (iv) $\leq 4.0$ mm; (v) $\leq 5.0$ mm; (vi) $\leq 6.0$ mm; (vii) $\leq 7.0$ mm; (viii) $\leq 8.0$ mm; (ix) $\leq 9.0$ mm; (x) $\leq 10.0$ mm; and (xi) >10.0 mm.

The stack or array of planar, plate or mesh electrodes preferably comprises a plurality or at least 2, 3, 4, 5, 6, 7, 8, 9, 10, 11, 12, 13, 14, 15, 16, 17, 18, 19 or 20 planar, plate or mesh electrodes wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use. At least some or at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are preferably supplied with an AC or RF voltage and wherein adjacent planar, plate or mesh electrodes are supplied with opposite phases of the AC or RF voltage.

The ion mobility spectrometer or separator preferably comprises a plurality of axial segments or at least 5, 10, 15, 20, 25, 30, 35, 40, 45, 50, 55, 60, 65, 70, 75, 80, 85, 90, 95 or 100 axial segments.

The apparatus may further comprise DC voltage means for maintaining a substantially constant DC voltage gradient along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator in order to urge at least some ions along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

The apparatus may further comprise transient DC voltage means arranged and adapted to apply one or more transient DC voltages or potentials or one or more transient DC voltage or potential waveforms to electrodes forming the ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

The apparatus may further comprise AC or RF voltage means arranged and adapted to apply two or more phase-shifted AC or RF voltages to electrodes forming the ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

The ion mobility spectrometer or separator preferably has an axial length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

The ion mobility spectrometer or separator preferably further comprises AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the electrodes forming the ion mobility spectrometer or separator in order to confine ions radially within the ion mobility spectrometer or separator.

The AC or RF voltage means is preferably arranged and adapted to supply an AC or RF voltage to the electrodes of the ion mobility spectrometer or separator having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak. The AC or RF voltage means is preferably arranged and adapted to supply an AC or RF voltage to the electrodes of the ion mobility spectrometer or separator having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

According to an embodiment, singly charged ions having a mass to charge ratio in the range of 1-100, 100-200, 200-300, 300-400, 400-500, 500-600, 600-700, 700-800, 800-900, 900-1000 or >1000 preferably have a drift or transit time through the ion mobility spectrometer or separator in the range: (i) 0-1 ms; (ii) 1-2 ms; (iii) 2-3 ms; (iv) 3-4 ms; (v) 4-5 ms; (vi) 5-6 ms; (vii) 6-7 ms; (viii) 7-8 ms; (ix) 8-9 ms; (x) 9-10 ms; (xi) 10-11 ms; (xii) 11-12 ms; (xiii) 12-13 ms; (xiv) 13-14 ms; (xv) 14-15 ms; (xvi) 15-16 ms; (xvii) 16-17 ms; (xviii) 17-18 ms; (xix) 18-19 ms; (xx) 19-20 ms; (xxi) 20-21 ms; (xxii) 21-22 ms; (xxiii) 22-23 ms; (xxiv) 23-24 ms; (xxv) 24-25 ms; (xxvi) 25-26 ms; (xxvii) 26-27 ms; (xxviii) 27-28 ms; (xxix) 28-29 ms; (xxx) 29-30 ms; (xxxi) 30-35 ms; (xxxii) 35-40 ms; (xxxiii) 40-45 ms; (xxxiv) 45-50 ms; (xxxv) 50-55 ms; (xxxvi) 55-60 ms; (xxxvii) 60-65 ms; (xxxviii) 65-70 ms; (xxxix) 70-75 ms; (xl) 75-80 ms; (xli) 80-85 ms; (xlii) 85-90 ms; (xliii) 90-95 ms; (xliv) 95-100 ms; and (xlv) >100 ms.

According to an embodiment, the apparatus further comprises a device arranged and adapted to maintain at least a portion of the ion mobility spectrometer or separator at a pressure selected from the group consisting of: (i) >0.001 mbar; (ii) >0.01 mbar; (iii) >0.1 mbar; (iv) >1 mbar; (v) >10 mbar; (vi) >100 mbar; (vii) 0.001-100 mbar; (viii) 0.01-10 mbar; and (ix) 0.1-1 mbar.

According to an embodiment, the apparatus further comprises a device arranged and adapted to maintain at least a portion of the ion mobility spectrometer or separator at a pressure selected from the group consisting of (i) <0.1 mbar; (ii) $\geq 0.1$ mbar; (iii) $\geq 0.2$ mbar; (iv) $\geq 0.3$ mbar; (v) $\geq 0.4$ mbar; (vi) $\geq 0.5$ mbar; (vii) $\geq 0.6$ mbar; (viii) $\geq 0.7$ mbar; (ix) $\geq 0.8$ mbar; (x) $\geq 0.9$ mbar; (xi) $\geq 1.0$ mbar; (xii) $\geq 1.1$ mbar; (xii) $\geq 1.2$ mbar; (xiv) $\geq 1.3$ mbar; (xv) $\geq 1.4$ mbar; (xvi) $\geq 1.5$ mbar; (xvii) $\geq 1.6$ mbar; (xviii) $\geq 1.7$ mbar; (xix) $\geq 1.8$ mbar; (xx) $\geq 1.9$ mbar; (xxi) $\geq 2.0$ mbar; (xxii) $\geq 3.0$ mbar;

(xxiii) ≧4.0 mbar; (xxiv) ≧5.0 mbar; (xxv) ≧6.0 mbar; (xxvi) ≧7.0 mbar; (xxvii) ≧8.0 mbar; (xxviii) ≧9.0 mbar; and (xxix) ≧10.0 mbar.

According to an embodiment, the apparatus further comprises a device arranged and adapted to maintain at least a portion of the ion mobility spectrometer or separator at a pressure selected from the group consisting of: (i) 0.1-0.5 mbar; (ii) 0.5-1.0 mbar; (iii) 1.0-1.5 mbar; (iv) 1.5-2.0 mbar; (v) 2.0-2.5 mbar; (vi) 2.5-3.0 mbar; (vii) 3.0-3.5 mbar; (viii) 3.5-4.0 mbar; (ix) 4.0-4.5 mbar; (x) 4.5-5.0 mbar; (xi) 5.0-5.5 mbar; (xii) 5.5-6.0 mbar; (xiii) 6.0-6.5 mbar; (xiv) 6.5-7.0 mbar; (xv) 7.0-7.5 mbar; (xvi) 7.5-8.0 mbar; (xvii) 8.0-8.5 mbar; (xviii) 8.5-9.0 mbar; (xix) 9.0-9.5 mbar; and (xx) 9.5-10.0 mbar.

The apparatus preferably further comprises a vacuum chamber which houses the first chamber and the second chamber. The vacuum chamber preferably comprises an entrance differential pumping aperture, an exit differential pumping aperture and a port connected to a vacuum pump.

The apparatus preferably further comprises one or more further ion guides arranged between the entrance differential pumping aperture and the first chamber and/or between the second chamber and the exit differential pumping aperture. The one or more further ion guides preferably have a length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

According to an embodiment, the one or more further ion guides may comprise:

(i) one or more multipole rod set or a segmented multipole rod sets;

(ii) one or more ion tunnels or ion funnels; or (iii) one or more stacks or arrays of planar, plate or mesh electrodes.

According to an embodiment, the apparatus further comprises means for pulsing ions into the ion mobility spectrometer or separator once every 0-5 ms, 5-10 ms, 10-15 ms, 15-20 ms, 20-25 ms, 25-30 ms, 30-35 ms, 35-40 ms, 40-45 ms, 45-50 ms, 50-55 ms, 55-60 ms, 60-65 ms, 65-70 ms, 70-75 ms, 75-80 ms, 80-85 ms, 85-90 ms, 90-95 ms, 95-100 ms or >100 ms.

According to another aspect of the present invention, there is provided a mass spectrometer comprising apparatus as described above.

The mass spectrometer preferably further comprises an ion source. The ion source is preferably selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption ionisation ("MALDI") ion source; (v) a Laser Desorption Ionisation ("LDI") ion source; (vi) an Atmospheric Pressure Ionisation ("API") ion source; (vii) a Desorption Ionisation On Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; and (xviii) a Thermospray ion source.

The ion source preferably comprises a pulsed or continuous ion source.

The mass spectrometer preferably further comprises a mass analyser. The mass analyser is preferably selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) an axial acceleration Time of Flight mass analyser.

The mass spectrometer preferably further comprises an ion detector.

According to another aspect of the present invention, there is provided a method comprising:

providing a first chamber;

providing a second chamber located downstream of the first chamber;

providing an ion mobility spectrometer or separator located in the second chamber;

providing a first gas or mixture of gases to the first chamber, the first gas or mixture of gases having a first average density or molecular weight $M_1$; and providing a second gas or mixture of gases to the second chamber, the second gas or mixture of gases having a second average density or molecular weight $M_2$, wherein $M_1<M_2$.

According to another aspect of the present invention, there is provided a method of mass spectrometry comprising a method as disclosed above.

According to another aspect of the present invention, there is provided an apparatus comprising:

a first chamber comprising an ion inlet aperture and a first gas outlet;

a second chamber located downstream of the first chamber, the second chamber comprising a second gas outlet and an ion outlet aperture;

an inter-chamber aperture between the first chamber and the second chamber;

an ion guide located in the first chamber;

an ion mobility spectrometer or separator located in the second chamber;

a device for providing a first gas or mixture of gases to the first chamber, the first gas or mixture of gases having a first average density or molecular weight $M_1$; and a device for providing a second gas or mixture of gases to the second chamber, the second gas or mixture of gases having a second average density or molecular weight $M_2$, wherein $M_2/M_1 \geq 4$.

The first chamber and the second chamber are preferably located within the same vacuum chamber. The vacuum chamber preferably comprises an entrance differential pumping aperture, an exit differential pumping aperture and a port connected to a vacuum pump.

According to another aspect of the present invention, there is provided a method comprising:

providing a first chamber comprising an ion inlet aperture and a first gas outlet;

providing a second chamber located downstream of the first chamber, the second chamber comprising a second gas outlet and an ion outlet aperture;

providing an inter-chamber aperture between the first chamber and the second chamber;

providing an ion guide located in the first chamber;

providing an ion mobility spectrometer or separator located in the second chamber;

providing a first gas or mixture of gases to the first chamber, the first gas or mixture of gases having a first average density or molecular weight $M_1$; and providing a second gas or mixture of gases to the second chamber, the second gas or mixture of gases having a second average density or molecular weight $M_2$, wherein $M_2/M_1 \geq 4$.

The method preferably further comprises locating the first chamber and the second chamber within the same vacuum chamber. The vacuum chamber preferably comprises an entrance differential pumping aperture, an exit differential pumping aperture and a port connected to a vacuum pump.

According to the preferred embodiment, helium gas is preferably provided in or to the first chamber. Helium gas is particularly advantageous since it results in low centre-of-mass collision energies with ions and hence ions entering the first chamber will preferably not be substantially fragmented. Furthermore, ions possess a relatively high ionic mobility as they pass through helium gas and hence ions will preferably not suffer from ion mobility discrimination effects. Therefore, according to an embodiment a relatively low strength electric field may be used to drive or inject ions into the chamber housing the ion mobility spectrometer and the possibility of undesired ion fragmentation and undesired ion mobility discrimination effects prior to ions entering the chamber housing the ion mobility spectrometer can be considerably reduced.

According to the preferred embodiment, the ion mobility spectrometer or separator is preferably provided at sub-atmospheric pressure. The ion mobility spectrometer or separator preferably exhibits good separation characteristics without use of excessively high gas pressures. The ion mobility spectrometer or separator preferably comprises a chamber which is divided into two sub-chambers which are preferably maintained at substantially the same pressure and which are preferably separated by an aperture. The first sub-chamber preferably predominantly contains a relatively light gas, such as helium, and preferably minimises ion fragmentation and/or discrimination effects as ions enter the first sub-chamber from a relatively low pressure chamber or region. The second sub-chamber preferably predominantly contains a relatively heavy gas, such as argon or nitrogen, and preferably provides good ion mobility separation characteristics for the ions.

BRIEF DESCRIPTION OF THE DRAWINGS

Various embodiments of the present invention together with an arrangement which is presented for illustration purposes will now be described, by way of example only, and with reference to the accompanying drawings in which.

DETAILED DESCRIPTION OF THE PREFERRED EMBODIMENTS

Figure 1:
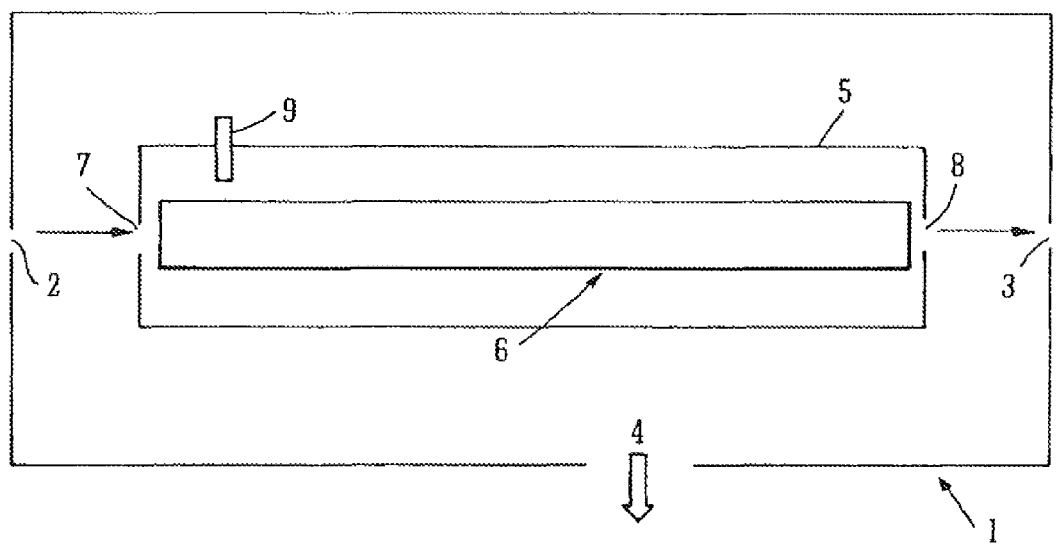
FIG. 1 shows a conventional ion mobility separator or spectrometer located in an IMS chamber which is maintained at sub-atmospheric pressure and wherein the IMS chamber is located within a differential vacuum chamber.

A section or portion of a conventional ion mobility spectrometer is shown in FIG. 1. A differential pumping chamber 1 is shown having an entrance differential pumping aperture 2 and an exit differential pumping aperture 3. An ion mobility spectrometer or separator 6 is provided within an IMS chamber 5. The IMS chamber 5 has an entrance 7 and an exit 8 and is located within the differential pumping chamber 1. Additional vacuum chambers (not shown) are located upstream and downstream of the differential pumping chamber 1 shown in FIG. 1.

The ion mobility spectrometer 6 is filled or supplied with gas via a gas outlet 9. The gas exits the IMS chamber 5 via both the entrance aperture 7 and the exit aperture 8 into the differential vacuum chamber 1 which surrounds the IMS chamber 5. The differential vacuum chamber 1 is pumped by a vacuum pump (not shown) which is connected to the differential vacuum chamber 1 via a port 4 in order to maintain the differential vacuum chamber 1 at a lower pressure than the pressure within the IMS chamber 5. Gas egress from the differential vacuum chamber 1 into adjoining vacuum chambers (not shown) is minimised through use of conductance limiting differential apertures 2, 3.

According to a known arrangement, ions pass from a relatively low pressure region upstream of the differential vacuum chamber 1 through the entrance differential pumping aperture 2 and into the differential vacuum chamber 1. The neutral gas in which ion mobility separation takes place is supplied to the IMS chamber 5 via the gas outlet 9. The gas which is supplied to the IMS chamber 5 exits through the entrance aperture 7 and the exit aperture 8 into the surrounding differential chamber 1. Ions entering the differential vacuum chamber 1 through the entrance differential aperture 2 therefore need to be driven into the IMS chamber 5 through the entrance aperture 7 against a significant outflow of relatively heavy gas which escapes from the IMS chamber 5 and which opposes the onward transmission of ions into the IMS chamber 5. Ions are driven into the IMS chamber 5 by arranging for the ions to have relatively high initial ion energies and by maintaining a relatively strong electric field between the entrance differential pumping aperture 2 and the ion mobility spectrometer 6 in order to urge ions into the IMS chamber 5.

Once ions have been urged into the IMS chamber 5, the ions then undergo ion mobility separation in the ion mobility spectrometer 6 which is located in the IMS chamber 5. Ions which have been separated according to their ion mobility emerge from the exit of the ion mobility spectrometer 6 and exit the IMS chamber 5 along with gas from the IMS chamber 5 via the exit aperture 8 into the differential vacuum chamber 1. The ions then exit the differential chamber 1 via the exit differential aperture 3. The ions are then onwardly transmitted to further sections of the mass spectrometer which are arranged downstream of the differential vacuum chamber 1 for further analysis and/or detection.

According to the known arrangement, ions are driven into the IMS chamber 5 against a backflow or outflow of the gas which is used or provided for ion mobility separation and may have a relatively high molecular weight. Ions may disadvantageously be caused to fragment as they are driven into the IMS chamber 5. Ions may also disadvantageously suffer from undesired ion mobility effects as the ions enter the IMS chamber 5. The ion mobility spectrometer 6 is operated or maintained at a relatively high pressure but this can put a relatively high demand on the vacuum pump requirement. Furthermore, relatively small entrance and exit apertures must be used and this can reduce ion transmission through the system.

Figure 2:
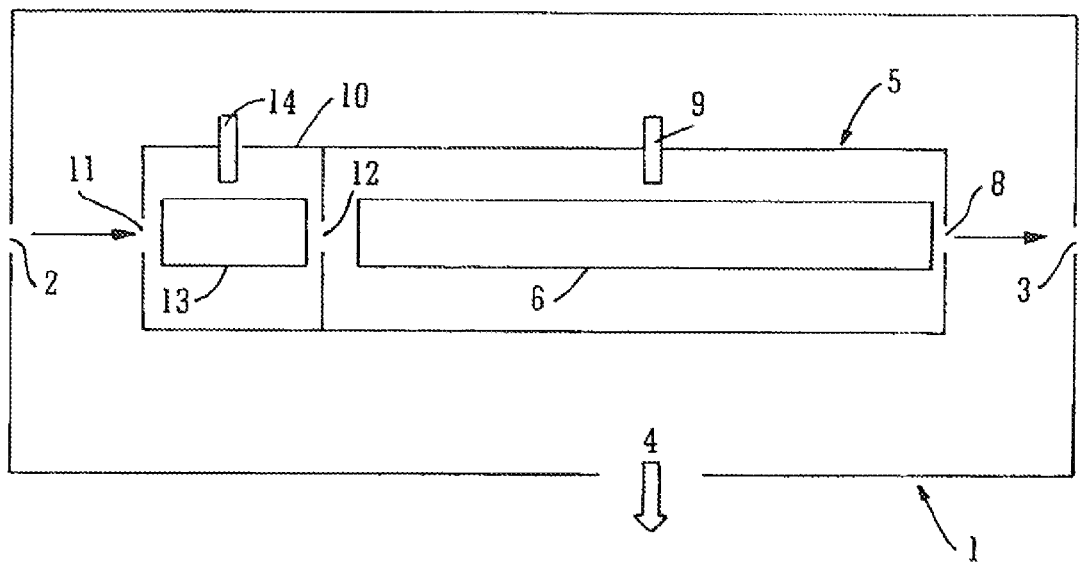
FIG. 2 shows an embodiment of the present invention wherein an ion mobility spectrometer or separator is arranged in a second chamber which is supplied with a relatively heavy gas such as argon or nitrogen and wherein a first chamber is arranged upstream which is supplied with a relatively light gas such as helium and wherein both the first and second chambers are located within a differential vacuum chamber.

FIG. 2 shows a section or portion of an ion mobility spectrometer according to a preferred embodiment of the present invention. An ion mobility spectrometer or separator 6 is provided within an IMS chamber 5. An injection chamber 10 having an entrance aperture 11 is preferably provided upstream of the IMS chamber 5. The injection chamber 10 is preferably connected to the IMS chamber 5 (or communicates with the IMS chamber 5) via an inter-chamber aperture 12. An ion guide 13 is preferably located or provided in the injection chamber 10. The ion guide 13 is preferably arranged to transportions efficiently from the inlet aperture 11 of the injection chamber 10 to the inter-chamber aperture 12 which is arranged between the injection chamber 10 and the IMS chamber 5. The ion guide 13 is therefore preferably arranged to transmit ions onwardly to the ion mobility spectrometer or separator 6.

The injection chamber 10 is preferably maintained at a given pressure and is supplied with a first gas or mixture of gases which is preferably emitted via or from a first gas outlet 14. The first gas or mixture of gases preferably exits the injection chamber 10 substantially through the entrance aperture 11 of the injection chamber 10.

The IMS chamber 5 is preferably maintained at a given pressure and is supplied with a second gas or mixture of gases which is preferably emitted via or from a second gas outlet 9. The second gas or mixture of gases preferably exits the IMS chamber 5 substantially through the exit aperture 8 of the IMS chamber 5.

The injection chamber 10 and the IMS chamber 5 are preferably housed or provided within the same differential vacuum chamber 1. The differential vacuum chamber 1 is preferably maintained at a pressure below that of the injection chamber 10 and that of the IMS chamber 5 by direct pumping by a vacuum pump (not shown) which is connected to the differential vacuum chamber 1 via port 4. Vacuum chambers (not shown) located upstream and downstream of the differential vacuum chamber 1 preferably have minimal gas loading from the differential vacuum chamber 1 due to conductance limiting entrance differential aperture 1 and conductance limiting exit differential aperture 3.

Ions preferably enter the differential vacuum chamber 1 via an entrance differential aperture 2. The ions are then preferably driven or urged into the injection chamber 10 via the entrance aperture 11. Ions are then preferably transmitted along and through the injection chamber 10 by being transmitted along an ion guide 13 arranged in the injection chamber 10. The ions then preferably pass from the injection chamber 10 to the IMS chamber 5 via the inter-chamber aperture 12. The ions are then preferably caused to pass along and through the ion mobility spectrometer or separator 6 which is arranged in the IMS chamber 5. The ions are preferably separated temporally as they pass along and through the ion mobility spectrometer or separator 6. The ions then preferably exit the ion mobility spectrometer or separator 6 and the IMS chamber 5 via the exit aperture 8. The ions are then preferably transmitted through the differential vacuum chamber 1 and preferably exit the differential vacuum chamber 1 via the exit differential aperture 3.

According to the preferred embodiment, the first gas or mixture of gases which preferably fills or which is supplied to the injection chamber 10 is preferably chosen such that minimal ion fragmentation and/or discrimination effects occur as ions are transmitted or injected into the injection chamber 10 and as the ions transit through the injection chamber 10. The first gas or mixture of gases preferably comprises helium gas although other gases may be used according to other less preferred embodiments.

The second gas or mixture of gases which preferably fills or which is supplied to the IMS chamber 5 is preferably chosen such that efficient ion mobility separation is preferably achieved within the ion mobility spectrometer or separator 6. The second gas or mixture of gases preferably comprises argon or nitrogen gas although other gases may be used according to other less preferred embodiments.

The flow rates of the first gas or mixture of gases and the second gas or mixture of gases into their respective chambers 10, 5 may be arranged such that the chamber pressures are substantially the same. Therefore, according to the preferred embodiment there may be essentially no net flow of gas through the inter-chamber aperture 12. To a first approximation at least, substantially all of the first gas or mixture of gases which is provided or supplied to the injection chamber 10 via the first gas outlet 14 may be considered as exiting the injection chamber 10 via the entrance aperture 11. Similarly, substantially all of the second gas or mixture of gases which is provided or supplied to the IMS chamber 5 via the second gas outlet 9 may be considered as exiting the IMS chamber 5 via the exit aperture 8.

In practice, there may be a small amount of diffusional mixing of gases at the inter-chamber aperture 5 or the boundary between the injection chamber 10 and the IMS chamber 5. Furthermore, slight imbalances in pressure between the two chambers 10, 5 may result in a small net gas flow from one chamber to the other. However, according to the preferred embodiment the degree of mixing of the first gas or mixture of gases and the second gas or mixture of gases is preferably minimal.

According to the preferred embodiment, one or more packets of ions which are desired to be separated according to their ion mobility preferably enter the differential vacuum chamber 1 from a relatively low pressure region via the conductance limiting entrance differential aperture 2. Ions are then preferably driven into the injection chamber 10 via the entrance aperture 11 against the outflow of the first gas or mixture of gases from the injection chamber 10. The ions may be driven into the injection chamber 10 by ensuring that the ions have a relatively high initial ion energy and/or by maintaining an appropriate electric field between the entrance differential aperture 2 and the injection chamber 10 which urges ions into the injection chamber 10. Ions in the injection chamber 10 are preferably confined and onwardly transmitted by the ion guide 13. The ions then preferably exit the ion guide 13 and preferably migrate or are otherwise transmitted through the first gas or mixture of gases and pass through the inter-chamber aperture 12. The ions preferably pass through the inter-chamber aperture 12 into the IMS chamber 5 which is preferably filled with the second gas or mixture of gases. The ions then preferably undergo ion mobility-based separation in the ion mobility spectrometer or separator 6 located within the IMS chamber 5. The mobility separated ions then preferably exit the ion mobility spectrometer or separator 6 and the IMS chamber 5 and preferably pass via the exit aperture 8 into the differential vacuum chamber 1. The ions are then preferably transmitted to the exit differential aperture 3 and the ions then preferably exit the differential vacuum chamber 1 to a lower pressure region via the conductance limiting exit differential aperture 3. The ions are then preferably onwardly transmitted for further analysis and/or detection. A mass analyser and ion detector is preferably located in a vacuum chamber (not shown) which is preferably arranged downstream of the differential vacuum chamber 1.

According to an embodiment, ions initially entering the differential vacuum chamber 1 may pass through a mass filtering device such as a quadrupole rod set operated as a band-pass device in an RF-only mode of operation or as a mass to charge ratio selective filter in an RF/DC mode of operation.

The ion guide 13 arranged in the injection chamber 10 preferably comprises a plurality of electrodes having apertures through which ions are transmitted in use. One or more transient DC voltages or potentials or one or more transient DC voltage or potential waveforms are preferably applied to the electrodes of the ion guide 13 in order to urge or propel ions along the length of the ion guide 13 by creating a plurality of real axial potential wells which are translated along the ion guide 13. Ions are preferably propelled through the interchamber aperture 12 by the application of the one or more transient DC voltages or potentials or the one or more transient DC voltage or potential waveforms to the electrodes forming the ion guide 13.

The ion mobility spectrometer or separator 6 preferably comprises a plurality of electrodes having apertures through which ions are transmitted in use. One or more transient DC voltages or potentials or one or more DC voltage or potential waveforms are preferably applied to the electrodes of the ion mobility spectrometer or separator 6 in order to urge ions along the length of the ion mobility spectrometer or separator 6. The gas pressure in the injection chamber 10 and/or in the IMS chamber 5 is preferably maintained in the range of 0.2 mbar to 2 mbar.

According to an embodiment, ions exiting the differential vacuum chamber 1 are preferably transmitted to a mass spectrometer such as a quadrupole mass filter, a linear or two dimensional quadrupole ion trap, a Paul or three dimensional quadrupole ion trap, a Time of Flight mass spectrometer, an orthogonal acceleration Time of Flight mass spectrometer, a Fourier Transform ICR mass spectrometer, a Fourier Transform Orbitrap mass spectrometer or a magnetic sector mass spectrometer.

Further embodiments are contemplated wherein other types of ion filtering/analysis may be employed prior to ions entering into the differential vacuum chamber 1.

The ion guide 13 in the injection chamber 10 may according to another embodiment comprise a multipole rod set ion guide or a DC-only ring stack ion guide. Axial DC electric fields may or may not be used to drive or urge ions along and through the first gas or mixture of gases present in the injection chamber 10.

The ion mobility spectrometer or separator 6 located in the IMS chamber 5 may according to one embodiment comprise a multipole rod set device or a DC-only stacked ring device. Axial DC voltage gradients may be used to effect ion mobility separation in the presence of the second gas or mixture of gases.

According to an embodiment, ions may enter the differential vacuum chamber 1 in a continuous stream or in a pulsed manner.

According to an embodiment, ions may be stored for a given time period in the ion guide 13 prior to being released in a gated manner into the IMS chamber 5.

According to an embodiment, one or more additional ion guides (not shown) may be arranged in the differential vacuum chamber 1 between the entrance differential aperture 2 and the entrance aperture 11 to the injection chamber 10.

According to an embodiment, one or more additional ion guides (not shown) may be arranged in the differential chamber 1 between the exit aperture 8 of the IMS chamber 5 and the exit differential aperture 3.

The one or more additional ion guides may be arranged to store and/or transport and/or manipulate ions.

Although the present invention has been described with reference to preferred embodiments, it will be apparent to those skilled in the art that various modifications in form and detail may be made without departing from the scope of the present invention as set forth in the accompanying claims.

The invention claimed is:

1. An apparatus comprising:
a first chamber;
a second chamber located downstream of the first chamber;
an ion guide including a plurality of electrodes located in the first chamber;
an ion mobility spectrometer or separator located in the second chamber;
a device for providing a first gas or mixture of gases to the first chamber, the first gas or mixture of gases having a first average density or molecular weight $M_1$;
a device for providing a second gas or mixture of gases to the second chamber, the second gas or mixture of gases having a second average density or molecular weight $M_2$, wherein $M_1 < M_2$; and
a device configured to maintain the first and second chambers at substantially the same pressure.

2. A method comprising:
filling a first chamber, within which is located an ion guide including a plurality of electrodes, with a first gas or mixture of gases having a first average density or molecular weight $M_1$; and
filling a second chamber, located downstream of the first chamber and within which is located an ion mobility spectrometer or separator, with a second gas or mixture of gases having a second average density or weight $M_2$, wherein $M_1 < M_2$ and the ratio $M_2/M_1$ is selected from the group consisting of: (i)$\geq$1.1; (ii)$\geq$1.5; (iii)$\geq$2.0; (iv)$\geq$3.0; (v)$\geq$4.0; (vi)$\geq$5.0; (vii)$\geq$6.0; (viii)$\geq$7.0; (ix)$\geq$8.0; (x)$\geq$9.0; (xi)$\geq$10.0; (xii)$\geq$11.0; (xiii)$\geq$12.0; (xiv)$\geq$13.0; (xv)$\geq$14.0; (xvi)$\geq$15.0; (xvii)$\geq$16.0; (xviii)$\geq$17.0; (xix)$\geq$18.0; (xx)$\geq$19.0; (xxi)$\geq$20.0; (xxii)$\geq$25.0; (xxiii)$\geq$30.0; (xxiv)$\geq$35.0; (xxv)$\geq$40.0; (xxvi)$\geq$45.0; (xxvii)$\geq$50.0; (xxviii)$\geq$55.0; (xxix)$\geq$60.0; (xxx)$\geq$65.0; and (xxxi)$\geq$70.0.

3. An apparatus comprising:
a first chamber;
a second chamber located downstream of the first chamber;
an ion guide including a plurality of electrodes located in the first chamber;
an ion mobility spectrometer or separator located in the second chamber;
a device for providing a first gas or mixture of gases to the first chamber, the first gas or mixture of gases having a first average density or molecular weight $M_1$, wherein the first gas or mixture of gases is provided at a pressure of 0.1-10.0 mbar; and
a device for providing a second gas or mixture of gases to the second chamber, the second gas or mixture of gases having a second average density or molecular weight $M_2$, wherein $M_1 < M_2$.

4. The apparatus as claimed in claim 3, wherein the ion guide includes a quadrupole rod set, a hexapole rod set, an octapole rod set or a rod set comprising more than eight rods.

5. The apparatus as claimed in claim 3, wherein the ion guide includes an ion tunnel or ion funnel having a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger or smaller in size or in area.

6. The apparatus as claimed in claim 3, wherein the ion guide includes a stack or array of planer, plate or mesh electrodes and further comprising an AC or RF voltage supply for supplying the plurality of planar, plate or mesh electrodes with an AC or RF voltage and wherein adjacent planar, plate or mesh electrodes are supplied with opposite phases of the AC or RF voltage.

7. The apparatus as claimed in claim 3, further comprising an AC or RF voltage supply configured to apply two or more phase-shifted AC or RF voltages to the plurality of electrodes forming the ion guide in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of an axial length of the ion guide.

8. The apparatus as claimed in claim 7, wherein the ion guide further comprises an AC or RF voltage supply configured to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the plurality of electrodes forming the ion guide in order to confine ions radially within the ion guide.

9. The apparatus as claimed in claim 3, wherein the ion guide is configured to collisionally cool, substantially thermalise or substantially reduce the kinetic energy of ions within the ion guide.

10. The apparatus as claimed in claim 3, wherein the ion mobility spectrometer or separator includes:
(i) a drift tube;
(ii) a multipole rod set or a segmented multipole rod set;
(iii) an ion tunnel or ion funnel; or
(iv) a stack or array of planar, plate or mesh electrodes.

11. The apparatus as claimed in claim 10, wherein the drift tube includes one or more electrodes and means for maintaining an axial DC voltage gradient or a substantially constant or linear axial DC voltage gradient along at least 5%, 10%, 15%, 20%, 25%, 30%, 35%, 40%, 45%, 50%, 55%, 60%, 65%, 70%, 75%, 80%, 85%, 90%, 95% or 100% of the axial length of the drift tube.

12. The apparatus as claimed in claim 10, wherein the multipole rod set comprises a quadrupole rod set, a hexapole rod set, an octapole rod set or a rod set comprising more than eight rods.

13. The apparatus as claimed in claim 10, wherein the ion tunnel or ion funnel includes a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger or smaller in size or in area.

14. The apparatus as claimed in claim 10, wherein the stack or array of planar, plate or mesh electrodes includes a plurality or at least 2, 3, 4, 5, 6, 7, 8, 9, 10, 11, 12, 13, 14, 15, 16, 17, 18, 19 or 20 planar, plate or mesh electrodes wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in a plane in which ions travel in use.

15. The apparatus as claimed in claim 14, wherein at least some or at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are supplied with an AC or RF voltage and wherein adjacent planar, plate or mesh electrodes are supplied with opposite phases of the AC or RF voltage.

16. The apparatus as claimed in claim 3, wherein the ion mobility spectrometer or separator comprises a plurality of axial segments or at least 5, 10, 15, 20, 25, 30, 35, 40, 45, 50, 55, 60, 65, 70, 75, 80, 85, 90, 95 or 100 axial segments.

17. The apparatus as claimed in claim 3, further comprising a DC voltage supply for maintaining a substantially constant DC voltage gradient along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator in order to urge at least some ions along at least a portion or at least 5%, 10%, 15%, 20%, 25%, 30%, 35%, 40%, 45%, 50%, 55%, 60%, 65%, 70%, 75%, 80%, 85%, 90%, 95% or 100% of an axial length of the ion mobility spectrometer or separator.

18. The apparatus as claimed in claim 3, further comprising a transient DC voltage supply configured to apply one or more transient DC voltages or potentials or one or more transient DC voltage or potential waveforms to electrodes forming the ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of an axial length of the ion mobility spectrometer or separator.

19. The apparatus as claimed in claim 3, further comprising an AC or RF voltage supply configured to apply two or more phase-shifted AC or RF voltages to electrodes forming the ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of an axial length of the ion mobility spectrometer or separator.

20. The apparatus as claimed in claim 3, wherein the ion mobility spectrometer or separator further comprises an AC or RF voltage supply configured to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the electrodes forming the ion mobility spectrometer or separator in order to confine ions radially within the ion mobility spectrometer or separator.

* * * * *